United States Patent [19]

Modi

[11] Patent Number: 5,417,982

[45] Date of Patent: May 23, 1995

[54] CONTROLLED RELEASE OF DRUGS OR HORMONES IN BIODEGRADABLE POLYMER MICROSPHERES

[76] Inventor: Pankaj Modi, 1298 Main St. W., Apt. 608, Hamilton, Ontario, Canada, L8S 1J4

[21] Appl. No.: 197,756

[22] Filed: Feb. 17, 1994

[51] Int. Cl.[6] .................................. A61K 9/14
[52] U.S. Cl. .................................. 424/486; 424/488;
424/489; 424/490; 424/492; 424/493; 424/494;
424/495; 424/496; 424/497; 514/964; 514/965
[58] Field of Search ............. 514/964, 965; 424/486,
424/488, 489, 490, 492, 496, 497, 493, 494, 495

[56] References Cited

U.S. PATENT DOCUMENTS

| | | | |
|---|---|---|---|
| 4,166,800 | 9/1979 | Fong | 424/490 |
| 4,272,398 | 6/1981 | Jaffe | 424/495 |
| 4,328,204 | 5/1982 | Wasserman et al. | 424/486 |
| 4,526,938 | 7/1985 | Churchill et al. | 525/415 |
| 4,622,244 | 11/1986 | Lapka et al. | 427/213.32 |
| 4,645,664 | 2/1987 | Lange | 528/354 |
| 4,675,189 | 6/1987 | Kent et al. | 514/963 |
| 4,832,686 | 5/1989 | Anderson | 604/49 |
| 4,897,267 | 1/1990 | Bontemps et al. | 424/489 |
| 4,904,479 | 2/1990 | Illum | 424/490 |
| 5,025,004 | 6/1991 | Wu et al. | 424/490 |
| 5,126,145 | 6/1992 | Evenstad et al. | 424/465 |
| 5,134,122 | 7/1992 | Orsolini | 514/15 |
| 5,187,150 | 2/1993 | Speiser et al. | 424/426 |
| 5,192,741 | 3/1993 | Orsolini et al. | 514/4 |
| 5,225,205 | 7/1993 | Orsolini | 424/489 |

*Primary Examiner*—Ronald W. Griffin

[57] ABSTRACT

A controlled release formulation for use with a variety of drugs or hormones are formed in microspherical form. The drug or hormone, e.g. bovine somatropine, is suspended in a polymer matrix. The polymer matrix is formed from at least two highly water soluble biodegradable polymers, selected for example from starch, crosslinked starch, ficoll, polysucrose, polyvinyl alcohol, gelatine, hydroxymethyl cellulose, hydroxyethyl cellulose, hydroxypropyl cellulose, hydroxypropylethyl cellulose, hydroxypropyl-methyl cellulose, sodium carboxymethyl cellulose, cellulose acetate, sodium alginate, polymaleic anhydride esters, polyortho esters, polyethyleneimine, polyethylene glycol, methoxypolyethylene glycol, ethoxypolyethylene glycol, polyethylene oxide, poly(1,3 bis(p-carboxyphenoxy) propane-co-sebacic anhydride, N,N-diethylaminoacetate, block copolymers of polyoxyethylene and polyoxypropylene. The microspheres are coated with a (d,1 lactide-glycolide) copolymer. The coating makes the microspheres more resistant to enzymatic degradation.

26 Claims, No Drawings

CONTROLLED RELEASE OF DRUGS OR HORMONES IN BIODEGRADABLE POLYMER MICROSPHERES

TECHNICAL FIELD

The present invention relates to an improved delivery system for the administration of drugs and hormones for use with animals, including humans.

BACKGROUND

It is known that many drugs and hormones, e.g. most peptidic and proteinic drugs are susceptible to degradation at the site of administration. In addition, some proteinic and peptidic drugs have very short in-vivo half lives. Consequently, multiple injections or multiple oral doses are required to achieve desirable therapy. It is desirable to increase the therapeutic efficacy of these drugs by using a controlled release delivery system. Attempts have been made to provide controlled release by means of tablets or capsules. However, none of these methods are entirely satisfactory. The present invention is intended to provide an oral or injection delivery system which is more cost efficient than previous methods and alleviates the aforementioned performance difficulties. The drug or hormone is sometimes referred to herein as the active ingredient.

DISCLOSURE OF INVENTION

Accordingly the present invention provides a controlled release formulation comprising biodegradable polymer microspheres wherein a drug or hormone is suspended in a polymer matrix, said polymer matrix being formed from at least two highly water soluble biodegradable polymers, and said microspheres being coated with a (d, l lactide-glycolide) copolymer.

In one embodiment the polymers are selected from the group consisting of starch, crosslinked starch, ficoll, polysucrose, polyvinyl alcohol, gelatine, hydroxymethyl cellulose, hydroxyethyl cellulose, hydroxypropyl cellulose, hydroxypropyl-ethyl cellulose, hydroxypropyl-methyl cellulose, sodium carboxymethyl cellulose, cellulose acetate, sodium alginate, polymaleic anhydride esters, polyortho esters, polyethyleneimine, polyethylene glycol, methoxypolyethylene glycol, ethoxypolyethylene glycol, polyethylene oxide,- poly(1,3 bis(p-carboxyphenoxy) propane-co-sebacic anhydride, N,N-diethylaminoacetate, block copolymers of polyoxyethylene and polyoxypropylene.

An example of a suitable polyortho ester is 3,9-bis(-methylene)-2,4,8,10,-tetra oxaspiro[5,5]undecane/1,6 hexanediol poly (ortho ester).

It is preferred that the weight ratio of the two polymers is in the range of from 20:80 to 80:20.

In another embodiment the polymer matrix is selected from starch and ficoll, starch and polysucrose, starch and polyvinyl alcohol, starch and gelatine, hydroxyethyl cellulose and hydroxypropyl cellulose, gelatine and hydroxyethyl cellulose, gelatine and polyvinyl alcohol, polysucrose and polyvinyl alcohol, and sodium carboxymethyl cellulose and sodium alginate.

When the polymer matrix comprises starch and ficoll, the preferred weight ratio of starch to ficoll is preferably from 85:15 to 60:40, and more preferably from 75:25 to 65:35.

When the polymer matrix comprises starch and polyvinyl alcohol, the preferred weight ratio of starch to polyvinyl alcohol is in the range of from 35:65 to 65:35, with a more preferred range of from 40:60 to 60:40. A microsphere having a starch to polyvinyl alcohol of about 50:50 is suitable for release of active ingredient over about a 10 day period. The starch has a tendency to degrade relatively quickly and the polyvinyl alcohol tends to give to the microsphere hardness and makes them more resistant to enzymatic degradation. Similar ratios are suitable for polysucrose and polyvinyl alcohol.

When the polymer matrix comprises one of the celluloses and ficoll, the preferred weight ratio of the cellulose to ficoll is in the range of from 80:20 to 65:35. Celluloses tend to give a soft and stable microsphere.

The selection of the particular (d, l lactide-glycolide) copolymer will depend in a large part on how long a period the microsphere is intended to release the active ingredient. For example, a (d, l lactide-glycolide) copolymer made from about 80% lactic acid and 20% glycolic acid is very stable and would provide a microsphere suitable for release of active ingredient over a period of weeks. A (d, l lactide-glycolide) copolymer made from 50% lactic acid and 50% glycolic acid is stable and would provide an microsphere suitable for release of active ingredient over a period of days. A (d, l lactide-glycolide) copolymer made from 20% lactic acid and 80% glycolic acid disintegrates relatively easily and would provide an microsphere suitable for release of active ingredient over a period of 1-2 days. The coating makes the microspheres more resistant to enzymatic degradation.

In another embodiment, the active ingredient is selected from bovine somatropine (sometimes referred to as BST), estrogens, androgens, insulin, insulin-like growth factors (sometimes referred to as IGF), interleukin-I, interleukin-II and cytokins. Two such cytokins are interferon-$\beta$ and interferon-$\gamma$.

The formulation is preferably in an oral form, although it may be in an injectable form.

A preferred hormone, to increase the milk production in cows, is BST.

The present invention also provides a process for making a controlled release formulation comprising microspheres of a drug or hormone suspended in a biodegradable polymer matrix polymer, said process comprising the steps of a) preparing an aqueous solution of at least two highly water soluble biodegradable polymers and adding thereto an active ingredient of a hormone or drug, b) mixing the solution and active ingredient with an emulsifying medium to form a homogenized microdroplet suspension, c) adding the homogenized microdroplet suspension slowly to a first organic solvent which contains a small concentration of a first surfactant, while stirring the microdroplet suspension and solvent, thus causing microspheres to precipitate, d) separating the microspheres from the first solvent and adding a solution of a (d,l lactide-glycolide) copolymer in a second organic solvent which contains a small concentration of a second surfactant, and e) slowly evaporating the solvent, leaving behind coated microspheres.

Step b) may be accomplished at room temperature or less but temperatures of $-5°$ C. to $10°$ C. are preferred with temperature in the range of from $0°$ C. to $5°$ C. being even more preferred. These temperature ranges are more suitable for the easy formation of the suspension.

The first organic solvent may be the same or different to the second organic solvent. A preferred first solvent is acetone and a preferred second solvent is an acetone and chloroform mixture.

Likewise the first surfactant may be the same or different to the second surfactant. Preferred surfactants are polyoxyethylene derivatives of fatty acid partial esters of sorbitol anhydrides, some of which are sold under the Tween trade mark. Preferred concentrations of surfactant are from 2 to 3% v/v of the solvent. At higher concentrations, the final microspheres tend to be irregular in shape.

In one embodiment the polymers are selected from the group consisting of starch, crosslinked starch, ficoll, polysucrose, polyvinyl alcohol, gelatine, hydroxymethyl cellulose, hydroxyethyl cellulose, hydroxypropyl cellulose, hydroxypropyl-ethyl cellulose, hydroxypropyl-methyl cellulose, sodium carboxymethyl cellulose, cellulose acetate, sodium alginate, polymaleic anhydride esters, polyortho esters, polyethyleneimine, polyethylene glycol, methoxypolyethylene glycol, ethoxypolyethylene glycol, polyethylene oxide,- poly(1,3 bis(p-carboxyphenoxy) propane-co-sebacic anhydride, N,N-diethylaminoacetate, block copolymers of polyoxyethylene and polyoxypropylene.

It is preferred that the weight ratio of the two polymers is in the range of from 20:80 to 80:20, with a more preferred range of from 40:60 to 60:40.

When the polymer matrix comprises starch and ficoll, the preferred weight ratio of starch to ficoll is preferably from 85:15 to 60:40, and more preferably from 75:25 to 65:35.

When the polymer matrix comprises starch and polyvinyl alcohol, the preferred weight ratio of starch to polyvinyl alcohol is in the range of from 35:65 to 65:35, with a more preferred range of from 40:60 to 60:40. A microsphere having a starch to polyvinyl alcohol of about 50:50 is suitable for release of active ingredient over about a 10 day period. Similar ratios are suitable for polysucrose and polyvinyl alcohol.

When the polymer matrix comprises one of the celluloses and ficoll, the preferred weight ratio of the cellulose to ficoll is in the range of from 80:20 to 65:35.

In another embodiment the polymer matrix is selected from starch and ficoll, starch and polysucrose, starch and polyvinyl alcohol, starch and gelatine, hydroxyethyl cellulose and hydroxypropyl cellulose, gelatine and hydroxyethyl cellulose, gelatine and polyvinyl alcohol, polysucrose and polyvinyl alcohol, and sodium carboxymethyl cellulose and sodium alginate.

In another embodiment, the active ingredient is selected from bovine somatropine, estrogens, androgens, insulin, insulin-like growth factors, interleukin-I, interleukin-II and cytokins. Two such cytokins are interferon-$\beta$ and interferon-$\gamma$.

A preferred hormone, to increase the milk production in cows, is BST.

In the first step of the process, the polymers which are intended to be used for the matrix are added to water, to form an aqueous solution, and the drug or hormone is added to the solution. This mixture is stirred and then mixed with an emulsifying medium, for example corn oil, rapeseed oil, vegetable oil. It is preferred that the amount of emulsifying medium exceed the amount of the polymer solution. For example, there may be as much as four times the amount of emulsifying medium as there is polymer solution. As indicated above, it is preferable that the mixture and emulsifying medium are held at a temperature lower than room temperature, and preferably between $-5°$ C. and $10°$ C., especially from about $0°$ C. to about $5°$ C. The polymer, water, emulsifying medium and drug or hormone are stirred or otherwise mixed until a coarse pre-emulsion is formed. The pre-emulsion is further homogenized to form a microdroplet suspension, for example by high speed mixing. In the laboratory, such high speed mixing can be accomplished by sonication. In commercial manufacture, a high speed blender or turbine mixer is preferred. In the third step, the microdroplet suspension preferably is poured slowly into a large amount of organic solvent such as acetone, containing a small concentration of surfactant, e.g. about 2% v/v Tween ® 80 surfactant, while stirring at high speed. Microspheres of the drug or hormone in the polymer matrix precipitate. The purpose of the surfactant is to prevent agglomeration of the polymer matrix, with consequent loss of microsphere-sized particles.

The particle size of the precipitate is in the order of 100 nm to 100 $\mu$m, more typically in the 10 nm to 10 $\mu$m range.

In the fourth step, the microspheres are further coated with a (d, l lactide-glycolide) copolymer by transferring the microspheres into a solution of the copolymer in a second organic solvent which contains a second surfactant. For example, the microspheres may be added to a 2% solution of (d, l lactide-glycolide) copolymer in a 1:1 acetone/chloroform mixture which contains 1% v/v Tween ® 80.

In the last step the second solvent and any remaining first solvent is removed by evaporation, so that a coating of (d, l lactide-glycolide) copolymer is left on the surface of the microspheres. A mild vacuum may be used to assist in the evaporation process.

The microspheres may then be made up in oral form or injectable form. The oral form is preferred. Clearly, the amounts and type of drug or hormone will depend on the treatment required and the human being or animal being treated.

An advantage of the microencapsulation is that it increases the in-vivo half lives of many peptidic and proteinic drugs or hormones, by providing protection against proteolytic or enzymatic degradation. Another advantage is that the therapeutic efficacies may be increased as a result of releasing the active ingredient in a controlled fashion over a prolonged period of time. A further advantage is prevention of degradation of the active ingredients when, in oral form, they pass through the gastrointestinal tract.

Microsphere formulations of the present invention which include BST may be used to increase milk production in cattle. Usually the formulation will be mixed with cattle feed and therefore will be taken orally. Such compositions may give high blood levels of BST over a long period of time, for example about 30 days, as a result of sustained release of natural or recombinant BST.

The present invention may be used to entrap other growth hormones in a polymer matrix, e.g. estrogens, androgens, insulin, IGF, interleukin-I and interleukin-II. Cytokins such as interferon-$\beta$ and interferon-$\gamma$, used in the treatment of diseases such as osteoporosis, diabetes mellitus and multiple sclerosis may also benefit from the present invention.

It will be understood by those skilled in the art that all of the ingredients must be suitable for ingestion by the animal. This means of course that toxic ingredients falling within the literal scope of the named chemical families mentioned herein would not be chosen.

The invention is illustrated by the following non-limiting examples.

EXAMPLE I 0.1 g starch was dissolved in 1 ml of dimethylsulphoxide (DMSO) and to this solution was added 0.5 g ethylhydroxycellulose and 0.1 g myoglobin protein dissolved in 1 ml water. The solution was stirred to make a homogenous solution. To this solution was added 10 ml vegetable oil at 0° C. and the resulting mixture was sonicated to form a microdroplet suspension. The microdroplet suspension was added slowly to 200 ml acetone containing 2% v/v Tween ® 80 surfactant. Microspheres were precipitated from the acetone. The acetone was decanted off and the microspheres were dried.

A 0.1 g sample of the microspheres was taken and the microspheres suspended in 3 ml of distilled water. This suspension was transferred to a UV cuvette. The absorbance of the myoglobin protein at 280 nm wavelength was observed over a period of 120 days and the percent of release of the myoglobin calculated. The results are shown in Table I.

TABLE I

| Time (Days) | % Myoglobin Released |
| --- | --- |
| 5 | 11 |
| 10 | 23 |
| 30 | 32 |
| 60 | 45 |
| 90 | 59 |
| 120 | 86 |

EXAMPLE II

The experiment of Example I was repeated except the myoglobin protein was replaced with flourescenated human serum albumine (FHSA). Although not normally used in animals, FHSA was used in this experiment to show the release characteristics. Animal drugs and hormones are expected to act in a similar manner. The absorbance of FHSA was monitored at 390 nm wavelength over a period of 90 days. The results are shown in Table II.

TABLE II

| Time (Days) | % FHSA Released |
| --- | --- |
| 1 | 9 |
| 2 | 11 |
| 3 | 20 |
| 7 | 23 |
| 11 | 31 |
| 30 | 38 |
| 60 | 54 |
| 90 | 92 |

I claim:

1. A controlled release formulation comprising biodegradable polymer microspheres wherein a drug or hormone is suspended in a polymer matrix, said polymer matrix being formed from at least two highly water soluble biodegradable polymers, and said microspheres being coated with a (d, l lactide-glycolide) copolymer.

2. A formulation according to claim 1 wherein the polymers are selected from the group consisting of starch, crosslinked starch, ficoll, polysucrose, polyvinyl alcohol, gelatine, hydroxymethyl cellulose, hydroxyethyl cellulose, hydroxypropyl cellulose, hydroxypropyl-ethyl cellulose, hydroxypropyl-methyl cellulose, sodium carboxymethyl cellulose, cellulose acetate, sodium alginate, polymaleic anhydride esters, polyethyleneimine, polyethylene glycol, methoxypolyethylene glycol, ethoxypolyethylene glycol, polyethylene oxide, poly(1,3 bis(p-carboxyphenoxy) propane-co-sebacic anhydride, N,N-diethylaminoacetate, block copolymers of polyoxyethylene and polyoxypropylene.

3. A formulation according to claim 1 wherein the weight ratio of the two polymers is in the range of from 20:80 to 80:20.

4. A formulation according to claim 3 wherein the polymer matrix is selected from starch and ficoll, starch and polysucrose, starch and polyvinyl alcohol, starch and gelatine, hydroxyethyl cellulose and hydroxypropyl cellulose, gelatine and hydroxyethyl cellulose, gelatine and polyvinyl alcohol, polysucrose and polyvinyl alcohol, ficoll and a member selected from the group consisting of hydroxymethyl cellulose, hydroxyethyl cellulose, hydroxypropyl cellulose, hydroxypropyl-ethyl cellulose, hydroxypropyl-methyl cellulose, sodium carboxymethyl cellulose and cellulose acetate, and sodium carboxymethyl cellulose and sodium alginate.

5. A formulation according to claim 4 wherein the polymer matrix comprises starch and ficoll and the weight ratio of starch to ficoll is from 80:20 to 60:40.

6. A formulation according to claim 5 wherein the weight ratio is from 75:25 to 65:35.

7. A formulation according to claim 4 wherein the polymer matrix comprises starch and polyvinyl alcohol and the weight ratio of starch to polyvinyl alcohol is in the range of from 35:65 to 65:35.

8. A formulation according to claim 7 wherein the weight ratio is from 40:60 to 60:40.

9. A formulation according to claim 4 wherein the polymer matrix comprises polysucrose and polyvinyl alcohol and the weight ratio of polysucrose to polyvinyl alcohol is from 35:65 to 65:35.

10. A formulation according to claim 4 wherein the polymer matrix comprises ficoll and a member selected from the group consisting of hydroxymethyl cellulose, hydroxyethyl cellulose, hydroxypropyl cellulose, hydroxypropyl-ethyl cellulose, hydroxypropyl-methyl cellulose, sodium carboxymethyl cellulose and cellulose acetate and the weight ratio of the cellulose to ficoll is in the range of from 80:20 to 65:35.

11. A formulation according to claim 1 wherein the active ingredient is selected from the group consisting of bovine somatropine, estrogens, androgens, insulin, insulin growth factors, interleukin-I, interleukin-II and cytokins.

12. A formulation according to claim 2 wherein the active ingredient is selected from the group consisting of bovine somatropine, estrogens, androgens, insulin, insulin growth factors, interleukin-I, interleukin-II and cytokins.

13. A process for making a controlled release formulation comprising microspheres of a drug or hormone suspended in a biodegradable polymer matrix polymer, said process comprising the steps of
   a) preparing an aqueous solution of at least two highly water soluble biodegradable polymers and adding thereto an active ingredient of a hormone or drug, b) mixing the solution and active ingredient with an emulsifying medium to form a homogenized microdroplet suspension, c) adding the homogenized microdroplet suspension slowly to a first organic solvent which contains a small concentration of a first surfactant, while stirring the microdroplet suspension and solvent, thus causing microspheres to precipitate, d) separating the microspheres from the first solvent and adding a solution of a (d,1 lactide-glycolide) copolymer in a second organic solvent which contains a small concentration of a second surfactant, and e) slowly evaporating the solvent, leaving behind coated microspheres.

14. A process according to claim 13 wherein the polymers used in step a) are selected from the group consisting of starch, crosslinked starch, ficoll, polysucrose, polyvinyl alcohol, gelatine, hydroxymethyl cellulose, hydroxyethyl cellulose, hydroxypropyl cellulose, hydroxypropyl-ethyl cellulose, hydroxypropyl-methyl cellulose, sodium carboxymethyl cellulose, cellulose acetate, sodium alginate, polymaleic anhydride esters, polyethyleneimine, polyethylene glycol, methoxypolyethylene glycol, ethoxypolyethylene glycol, polyethylene oxide,poly(1,3 bis(p-carboxyphenoxy) propane-co-sebacic anhydride, N,N-diethylaminoacetate, block copolymers of polyoxyethylene and polyoxypropylene.

15. A process according to claim 13 wherein the weight ratio of the two polymers used in step a) is in the range of from 20:80 to 80:20.

16. A process according to claim 15 wherein the polymer matrix is selected from starch and ficoll, starch and polysucrose, starch and polyvinyl alcohol, starch and gelatine, hydroxyethyl cellulose and hydroxypropyl cellulose, gelatine and hydroxyethyl cellulose, gelatine and polyvinyl alcohol, polysucrose and polyvinyl alcohol, and sodium carboxymethyl cellulose ficoll and a member selected from the group consisting of hydroxymethyl cellulose, hydroxyethyl cellulose, hydroxypropyl cellulose, hydroxypropyl-ethyl cellulose, hydroxypropyl-methyl cellulose, sodium carboxymethyl cellulose and cellulose acetate and sodium alginate.

17. A process according to claim 16 wherein the polymer matrix comprises starch and ficoll and the weight ratio of starch to ficoll is from 80:20 to 60:40.

18. A process according to claim 17 wherein the weight ratio is from 75:25 to 65:35.

19. A process according to claim 16 wherein the polymer matrix comprises starch and polyvinyl alcohol and the weight ratio of starch to polyvinyl alcohol is in the range of from 35:65 to 65:35.

20. A process according to claim 19 wherein the weight ratio is from 40:60 to 60:40.

21. A process according to claim 16 wherein the polymer matrix comprises polysucrose and polyvinyl alcohol and the weight ratios of polysucrose to polyvinyl alcohol is from 35:65 to 65:35.

22. A process according to claim 16 wherein the polymer matrix comprises ficoll and a member selected from the group consisting of hydroxymethyl cellulose, hydroxyethyl cellulose, hydroxypropyl cellulose, hydroxypropyl-ethyl cellulose, hydroxypropyl-methyl cellulose, sodium carboxymethyl cellulose and cellulose acetate and the weight ratio of the cellulose to ficoll is in the range of from 80:20 to 65:35.

23. A process according to claim 13 wherein the active ingredient is selected from the group consisting of bovine somatropine, estrogens, androgens, insulin, insulin growth factors, interleukin-I, interleukin-II and cytokins.

24. A process according to claim 14 wherein the active ingredient is selected from the group consisting of bovine somatropine, estrogens, androgens, insulin, insulin growth factors, interleukin-I, interleukin-II and cytokins.

25. A method for the treatment of animals or humans wherein a controlled release formulation is administered to the animal or human being, wherein the formulation comprises biodegradable polymer microspheres wherein a drug or hormone, which is suitable for administration to animals, is suspended in a polymer matrix, said polymer matrix being formed from at least two highly water soluble biodegradable polymers, and said microspheres being coated with a (d, 1 lactide-glycolide) copolymer.

26. A method according to claim 25 wherein an increase in milk production of a cow is assisted by the controlled release of bovine somatropine, said bovine somatropine being administered in the form of biodegradable polymer microspheres, said bovine somatropine being suspended in an a polymer matrix formed from at least two highly water soluble biodegradable polymers selected from the group consisting of starch, crosslinked starch, ficoll, polysucrose, polyvinyl alcohol, gelatine, hydroxy-methyl cellulose, hydroxyethyl cellulose, hydroxypropyl cellulose, hydroxypropyl-ethyl cellulose, hydroxypropyl-methyl cellulose, sodium carboxymethyl cellulose, cellulose acetate, sodium alginate, polymaleic anhydride esters, polyethyleneimine, polyethylene glycol, methoxypolyethylene glycol, ethoxypolyethylene glycol, polyethylene oxide,poly(1,3 bis(p-carboxyphenoxy) propane-co-sebacic anhydride, N,N-diethylaminoacetate, block copolymers of polyoxyethylene and polyoxypropylene, and said microspheres being coated with a (d, 1 lactide-glycolide) copolymer.

* * * * *